(12) United States Patent
Clark et al.

(10) Patent No.: US 7,378,360 B2
(45) Date of Patent: May 27, 2008

(54) WATER DISPERSIBLE, PRE-SATURATED WIPING PRODUCTS

(75) Inventors: James W. Clark, Roswell, GA (US); Joseph Mitchell, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 136 days.

(21) Appl. No.: 10/739,873

(22) Filed: Dec. 17, 2003

(65) Prior Publication Data

US 2005/0136780 A1 Jun. 23, 2005

(51) Int. Cl.
*D04H 1/00* (2006.01)
*D04H 13/00* (2006.01)
*B32B 3/00* (2006.01)
*B32B 5/26* (2006.01)

(52) U.S. Cl. ............... 442/414; 442/59; 442/327; 442/382; 442/415; 442/416

(58) Field of Classification Search .......... 442/59, 442/327, 328, 414, 415, 416, 11, 13, 35, 43, 442/58, 96, 118, 166; 428/235, 236, 245, 428/96

See application file for complete search history.

(56) References Cited

U.S. PATENT DOCUMENTS

| | | | |
|---|---|---|---|
| 2,402,469 A * | 6/1946 | Toland et al. ............ 162/168.1 |
| 3,282,776 A | 11/1966 | Kitzke et al. | |
| 3,287,214 A | 11/1966 | Taylor et al. | |
| 3,445,564 A | 5/1969 | Kirschner | |
| 3,563,241 A * | 2/1971 | Evans et al. ................. 604/364 |
| 3,610,245 A | 10/1971 | Bernardin et al. | |
| 3,616,797 A | 11/1971 | Champaigne, Jr. et al. | |
| 3,635,221 A | 1/1972 | Champaigne, Jr. | |
| 3,654,928 A | 4/1972 | Duchane | |
| 3,881,210 A | 5/1975 | Drach et al. | |
| 4,033,918 A | 7/1977 | Hauber | |
| 4,201,764 A | 5/1980 | French et al. | |
| 4,210,633 A | 7/1980 | Takruri et al. | |
| 4,258,849 A | 3/1981 | Miller | |
| 4,283,421 A | 8/1981 | Ray | |
| 4,372,311 A | 2/1983 | Potts | |
| 4,540,505 A | 9/1985 | Frazier | |
| 4,570,311 A * | 2/1986 | Kawamura et al. ........... 28/164 |
| 4,575,891 A | 3/1986 | Valente | |
| 4,639,390 A * | 1/1987 | Shoji ..................... 428/195.1 |
| 4,666,647 A | 5/1987 | Enloe et al. | |
| 4,755,421 A | 7/1988 | Manning et al. | |
| 4,761,258 A | 8/1988 | Enloe | |
| 4,990,339 A | 2/1991 | Scholl et al. | |
| 4,998,984 A | 3/1991 | McClendon | |
| 5,092,013 A | 3/1992 | Genovese, Jr. | |
| 5,145,663 A | 9/1992 | Simmons | |
| 5,158,844 A * | 10/1992 | Hagens et al. .............. 429/249 |
| 5,166,263 A | 11/1992 | Ohgi et al. | |
| 5,181,966 A | 1/1993 | Honeycutt et al. | |
| 5,181,967 A | 1/1993 | Honeycutt | |
| 5,207,837 A | 5/1993 | Honeycutt | |
| 5,208,104 A | 5/1993 | Ueda et al. | |
| 5,252,332 A | 10/1993 | Goldstein | |
| 5,256,417 A | 10/1993 | Koltisko | |
| 5,264,269 A | 11/1993 | Kakiuchi et al. | |
| 5,268,222 A | 12/1993 | Honeycutt | |
| 5,281,306 A | 1/1994 | Kakiuchi et al. | |
| 5,342,335 A | 8/1994 | Rhim | |
| 5,441,723 A | 8/1995 | Simmons | |
| 5,445,785 A | 8/1995 | Rhim | |
| 5,455,114 A | 10/1995 | Ohmory et al. | |
| 5,470,653 A | 11/1995 | Honeycutt et al. | |
| 5,473,789 A | 12/1995 | Oster | |
| 5,486,418 A | 1/1996 | Ohmory et al. | |
| 5,500,068 A | 3/1996 | Srinivasan et al. | |
| 5,500,281 A | 3/1996 | Srinivasan et al. | |
| 5,508,101 A | 4/1996 | Patnode et al. | |
| 5,509,913 A * | 4/1996 | Yeo ............................ 604/364 |
| 5,527,845 A | 6/1996 | Strelow et al. | |
| 5,567,510 A | 10/1996 | Patnode et al. | |
| 5,599,872 A | 2/1997 | Sulewski | |
| 5,620,786 A | 4/1997 | Honeycutt et al. | |
| 5,630,972 A | 5/1997 | Patnode et al. | |

(Continued)

FOREIGN PATENT DOCUMENTS

CA 2093051 6/1994

(Continued)

OTHER PUBLICATIONS

Abstract of German Patent DE3227065, Jan. 26, 1984.

(Continued)

*Primary Examiner*—Norca Torres-Velazquez
(74) *Attorney, Agent, or Firm*—Dority & Manning, P.A.

(57) ABSTRACT

A water dispersible nonwoven web is disclosed. The nonwoven web is produced in an airlaying process and contains pulp fibers mixed with water soluble fibers. The water soluble fibers may be, for instance, polyvinyl alcohol fibers. The nonwoven web may be pre-saturated with a cleaning solution. Once pre-saturated with a cleaning solution, the wiping product is particularly well suited to cleaning and/or disinfecting surfaces, such as toilet seats prior to use. Because the nonwoven web is water dispersible, the wiper may be disposed of by being flushed down a toilet.

48 Claims, 2 Drawing Sheets

U.S. PATENT DOCUMENTS

| | | | |
|---|---|---|---|
| 5,641,567 A | 6/1997 | Brown et al. | |
| 5,650,219 A | 7/1997 | Honeycutt | |
| 5,656,361 A | 8/1997 | Vogt et al. | |
| 5,658,977 A | 8/1997 | Yang et al. | |
| 5,665,824 A | 9/1997 | Chang et al. | |
| 5,728,404 A | 3/1998 | von Rheinbaben et al. | |
| 5,735,812 A | 4/1998 | Hardy | |
| 5,762,948 A | 6/1998 | Blackburn et al. | |
| 5,763,065 A | 6/1998 | Patnode et al. | |
| 5,783,505 A * | 7/1998 | Duckett et al. | 442/411 |
| 5,830,488 A | 11/1998 | Suzuki et al. | |
| 5,840,633 A | 11/1998 | Kurihara et al. | |
| 5,871,679 A | 2/1999 | Honeycutt | |
| 5,916,678 A | 6/1999 | Jackson et al. | |
| 5,935,880 A | 8/1999 | Wang et al. | |
| 5,947,917 A | 9/1999 | Carté et al. | |
| 5,948,710 A | 9/1999 | Pomplun et al. | |
| 5,952,251 A | 9/1999 | Jackson et al. | |
| 5,952,420 A | 9/1999 | Senkus et al. | |
| 5,986,004 A | 11/1999 | Pomplun et al. | |
| 6,112,385 A | 9/2000 | Fleissner et al. | |
| 6,123,966 A | 9/2000 | Kross | |
| 6,126,931 A | 10/2000 | Sawan et al. | |
| 6,146,587 A | 11/2000 | Morgan | |
| 6,202,259 B1 | 3/2001 | Burr et al. | |
| 6,319,863 B1 * | 11/2001 | Takeuchi et al. | 442/155 |
| 6,346,279 B1 | 2/2002 | Rochon | |
| 6,380,152 B1 * | 4/2002 | Julemont et al. | 510/438 |
| 6,420,284 B1 * | 7/2002 | Myers et al. | 442/166 |
| 6,451,718 B1 | 9/2002 | Yamada et al. | |
| 6,552,123 B1 | 4/2003 | Katayama et al. | |
| 6,576,575 B1 | 6/2003 | Griesbach, III et al. | |
| 2002/0180092 A1 | 12/2002 | Abba et al. | |

FOREIGN PATENT DOCUMENTS

| | | |
|---|---|---|
| CA | 2111173 A1 | 2/1995 |
| EP | 0726068 A2 | 8/1996 |
| EP | 0945536 A2 | 9/1999 |
| GB | 2254626 A | 10/1992 |
| GB | 2284820 A | 6/1995 |
| GB | 2295553 A | 6/1996 |
| JP | 2001355170 | 12/2001 |
| WO | WO 9425189 A1 | 11/1994 |
| WO | WO 9702375 A1 | 1/1997 |
| WO | WO 9744512 A1 | 11/1997 |
| WO | WO 9841577 A1 | 9/1998 |
| WO | WO 0058539 A1 | 10/2000 |
| WO | WO 0061851 A1 | 10/2000 |
| WO | WO 0131103 A2 | 5/2001 |
| WO | WO 0131103 A3 | 5/2001 |

OTHER PUBLICATIONS

Abstract of Japanese Patent JP2074694, Mar. 14, 1990.
Abstract of Japanese Patent JP2082925, Mar. 23, 1990.
Abstract of Japanese Patent JP3076900, Apr. 2, 1991.
Abstract of Japanese Patent JP3113099, May 14, 1991.
Abstract of Japanese Patent JP5321105, Dec. 7, 1993.
Abstract of Japanese Patent JP8158224, Jun. 18, 1996.
Search Report and Written Opinion for PCT/US2004/016424, Dec. 22, 2004.

* cited by examiner

WATER DISPERSIBLE, PRE-SATURATED WIPING PRODUCTS

BACKGROUND OF THE INVENTION

Saturated or pre-moistened wiping products have been used in a variety of wiping and polishing applications. Perhaps the most common form is a stack of individual, folded sheets packaged in a plastic container for use as baby wipes. Wet wipes are also available containing antimicrobial compositions for cleaning desired surfaces. Wet wipes are typically used only once and then discarded.

Wet wipes designed to clean or disinfect adjacent surfaces are typically made containing synthetic fibers and/or water insoluble adhesives or binders. For instance, many wet wipe materials are made from airlaid webs that have been treated with a water insoluble adhesive or spunlace webs containing water insoluble synthetic fibers. Wet wipe materials may also contain meltspun webs, such as meltblown webs, spunbond webs and laminates thereof. Although these materials have good strength properties, the materials generally are not water dispersible, meaning that the materials do not disintegrate when immersed in water. Thus, the materials are not biodegradable and must be thrown into a trash receptacle after use.

Thus, a need currently exists for a pre-saturated wiping product that is designed to disinfect and clean surfaces, while also being water dispersible and/or biodegradable. More particularly, a need exists for a pre-saturated wiping product that sanitizes surfaces, such as a toilet seat, and then can be flushed safely down a toilet.

SUMMARY OF THE INVENTION

In general, the present invention is directed to wet wipes that are particularly well suited for cleaning surfaces, such as toilet seats, bathtubs, sinks, walls, and the like. The wet wipes are water dispersible meaning that the wet wipes will disintegrate when immersed in water. Thus, after use, the wet wipes may be disposed by being flushed down a toilet.

In one embodiment, the present invention is directed to a nonwoven material that is well suited to being saturated with a cleaning solution for use as a wet wipe. The nonwoven material comprises a nonwoven airlaid fibrous web. The airlaid web comprises pulp fibers and water soluble fibers. The water soluble fibers comprise polyvinyl alcohol. The water soluble fibers are substantially soluble in water at a temperature less than about 50° C., such as less than about 37° C. In one embodiment, for instance, the water soluble fibers are substantially soluble in water at a temperature of less than about 10° C. The water soluble fibers are present in the airlaid web in an amount sufficient to make the web water dispersible.

The water soluble fibers may have an average fiber length of less than about 8 mm, such as from about 2 mm to about 8 mm. The water soluble fibers may be incorporated into the nonwoven airlaid fibrous web such that they are bonded with the pulp fibers. In one embodiment, the airlaid fibrous web is embossed.

The polyvinyl alcohol used to make the water soluble fibers may be partially hydrolyzed. For instance, the polyvinyl alcohol may be less than about 95% hydrolyzed, such as less than about 90% hydrolyzed. By being partially hydrolyzed, the polyvinyl alcohol may contain vinyl acetate units. For many applications, the polyvinyl alcohol should be hydrolyzed by at least 80%.

The pulp fibers may be homogenously mixed with the water soluble fibers. The pulp fibers may be, for instance, softwood fibers. The water soluble fibers may be present in the airlaid fibrous web in an amount from about 10% to about 80% by weight, such as from about 15% to about 35% by weight. The airlaid fibrous web may have a basis weight of from about 20 gsm to about 120 gsm, such as from about 40 gsm to about 80 gsm.

In order to form a water dispersible, pre-saturated wiping product, the above described nonwoven airlaid fibrous web may be impregnated with a cleaning solution. The cleaning solution may comprise, for instance, alcohol and water. Alcohol may be present in the solution in an amount greater than about 60% by weight, such as from about 70% to about 90% by weight. The alcohol may be ethyl alcohol or isopropyl alcohol.

In addition to alcohol and water, the cleaning solution may contain further additives. For instance, the cleaning solution may contain a glycol or a glyceride.

In other embodiments, the cleaning solution may contain an anti-microbial agent and a fragrance.

The water dispersible, pre-saturated wiping products may be contained in a resealable container. The wiping products may comprise individual sheets that are stacked within the container. Alternatively, the individual sheets may be spirally wound into a roll and separated by perforations.

Other features and aspects of the present invention are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
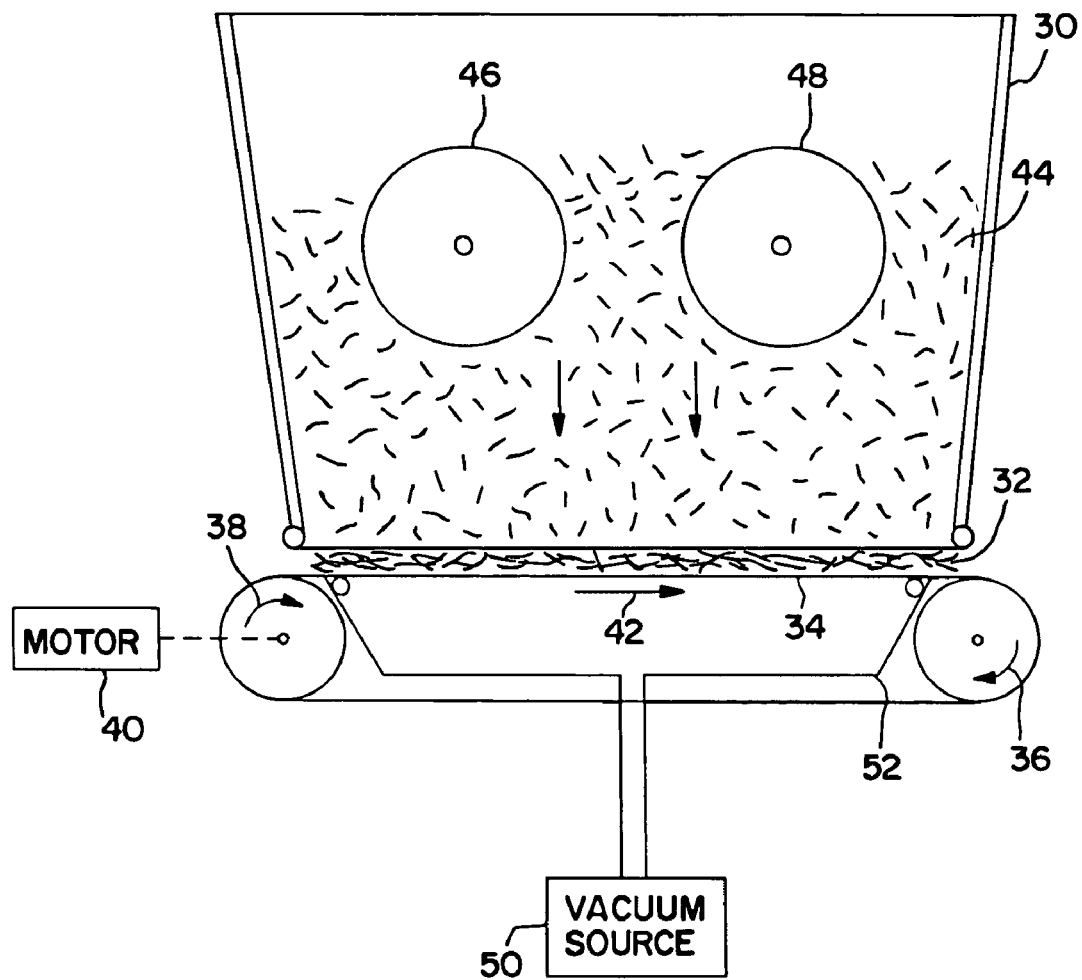
FIG. 1 is a simplified cross-sectional view of one embodiment of an airlaying apparatus that may be used to form nonwoven webs in accordance with the present invention.

Repeated use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended in limiting the broader aspects of the present invention, which broader aspects are embodied in the exemplary construction.

In general, the present invention is directed to nonwoven webs that are water dispersible. The nonwoven webs may be formed in an airlaying process. The webs have been found to be particularly well suited for use as wiping products. For instance, the webs may be pre-saturated with a cleaning solution and used as a disposable wipe for cleaning and disinfecting surfaces.

For example, in one embodiment, the water dispersible, pre-saturated wiping products may be contained in a resealable container that is either mounted to a surface, such as a wall, or configured to be portable. The wiping products may be dispensed from the container one at a time and used for cleaning and disinfecting. For example, the wiping products may be used for cleaning household or commercial surfaces such as toilets, bathtubs, sinks, walls, eating tables, and the like. In one particular embodiment, the wiping products may be used to wipe a toilet seat prior to use. Because the wiping product is water dispersible, the wiping product may then be disposed of by being flushed down the toilet.

The water dispersible, pre-saturated wiping products may be carried by individuals for personal use. Alternatively, the wiping products may be provided by commercial establishments in their bathrooms for use by their patrons and by janitors.

The water dispersible, pre-saturated wiping product of the present invention generally comprises a nonwoven fibrous web impregnated with a cleaning solution. The nonwoven fibrous web may be an airlaid web. The airlaid web contains pulp fibers mixed with water soluble fibers. The water soluble fibers are bonded to the pulp fibers. When the nonwoven material is immersed in water, the water soluble fibers break down and solubilize causing the fibrous web to disintegrate.

In one embodiment, the water soluble fibers comprise polyvinyl alcohol fibers. Polyvinyl alcohol is a synthetic polymer that may be formed, for instance, by replacing acetate groups in polyvinyl acetate with hydroxyl groups according to a hydrolysis reaction. The basic properties of polyvinyl alcohol depend on its degree of polymerization, degree of hydrolysis, and distribution of hydroxyl groups. In terms of the degree of hydrolysis, polyvinyl alcohol may be produced so as to be fully hydrolyzed or partially hydrolyzed.

The water solubility of polyvinyl alcohol depends primarily on its degree of polymerization and degree of hydrolysis. Of the two factors, the degree of hydrolysis has more of an effect on water solubility. For instance, the presence of small amounts of residual acetate units (such as little as 2-3 mole percent) causes a significant change in the solubility of the polymer.

In general, the water soluble fibers should be capable of substantially dissolving when immersed in water at a temperature that is consistent with the tap water temperature of where the product is to be used. Thus, the water soluble fibers should substantially dissolve in water at a temperature of less than about 50° C., such as less than about 37° C. In other embodiments, the fibers should be capable of dissolving in water at a temperature of less than about 20° C., such as less than about 15° C. or less than about 10° C. In colder climates, tap water temperatures may be less than 5° C. during the winter months. Thus, in still another embodiment of the present invention, the water soluble fibers may be capable of being dissolved in water at a temperature of less than about 5° C., such as less than about 2° C.

As described above, hydrolysis plays a major role in determining the solubility of polyvinyl alcohol fibers. Thus, in one embodiment, the water soluble fibers are made from polyvinyl alcohol that is less than 95% hydrolyzed, such as less than about 90% hydrolyzed. For example, in one embodiment, the polyvinyl alcohol may be hydrolyzed in an amount of from about 80% to about 95%. As used herein, the above percentages are based upon a mole percent.

In addition to controlling the amount of hydrolysis, polyvinyl alcohol fibers may also be made water soluble by other means. For instance, it is also possible to obtain a fiber soluble in water at a temperature lower than about 50° C. by using a polyvinyl alcohol polymer containing units other than those from vinyl alcohol or vinyl acetate. In particular, the polyvinyl alcohol polymer may be chemically modified by incorporating into the polymer various monomers. The monomers may be present, for instance, in an amount of less than about 5 mole percent, such as from about 0.1 mole percent to about 2 mole percent.

Examples of monomers that may be incorporated into a polyvinyl alcohol polymer for increasing the water solubility of the polymer include ethylene, allyl alcohol, itaconic acid, acrylic acid, maleic anhydride, arylsulfonic acid, and vinyl esters of aliphatic acids having at least four carbon atoms such as vinyl pivalate, vinyl pyrrolidone and compounds obtained by neutralizing part or all of the above ionic groups. The monomers may be introduced into the polymer by copolymerization or by post-reaction, and may be distributed in the resulting polymer chain in random, blockwise or grafted form with no specific limitation.

Examples of water soluble fibers that may be used in the present invention are disclosed in U.S. Pat. Nos. 5,207,837, 5,455,144, 5,952,251 and 6,552,123, which are all incorporated by reference. Commercially available water soluble polyvinyl alcohol fibers are available from the Kuraray Company of Japan. For example, in one particular embodiment, WN2 fibers obtained from the Kuraray Company are used to form airlaid nonwoven webs in accordance with the present invention.

In general, the polyvinyl alcohol fibers have a fiber length and diameter that are suitable for use in an airforming process and form a nonwoven web when combined with pulp fibers. For instance, the polyvinyl alcohol fibers may have an average fiber length of from about 2 mm to about 8 mm, such as from about 2 mm to about 6 mm. The diameter of the fibers may be, for instance, from about 2 to about 4 detex.

The water soluble fibers are contained in the airlaid nonwoven web in an amount sufficient for the web to be dispersible when immersed in water, such that the web breaks down and disintegrates. For example, in one embodiment, the water soluble fibers are present in the airlaid web in an amount of at least 10% by weight, such as in an amount of at least 15% by weight. In other embodiments, the water soluble fibers are present in the airlaid web in an amount of at least 20% by weight, such as at least 25% by weight. The upper limit of water soluble fibers present in the airlaid web is generally not critical. Since pulp fibers are generally less expensive than the water soluble fibers, however, the water soluble fibers for most applications are present in an amount of less than about 80% by weight, such as less than about 50% by weight.

As described above, the water soluble fibers are mixed with pulp fibers in forming the airlaid web. The pulp fibers may be any suitable paper making fibers. For instance, the fibers can comprise softwood fibers. The softwood fibers can be Northern softwood kraft fibers or Southern softwood kraft fibers. Cotton fibers, rayon fibers and recycled fibers may also be present. If desired, hardwood fibers may also be contained in the nonwoven web in smaller amounts. The fibers can also be treated with a debonder prior to being formed into the airlaid web.

One embodiment of a process for forming airlaid webs in accordance with the present invention will now be described in detail with particular reference to FIGS. 1 and 2. Referring to FIG. 1, an airlaying forming station 30 is shown which produces a non-woven web 32 on a forming fabric or screen 34. The forming fabric 34 can be in the form of an endless belt mounted on support rollers 36 and 38. A suitable driving device, such as an electric motor 40 rotates at least one of the support rollers 38 in a direction indicated by the arrows at a selected speed. As a result, the forming fabric 34 moves in a machine direction indicated by the arrow 42.

The forming fabric 34 can be provided in other forms as desired. For example, the forming fabric can be in the form of a circular drum which can be rotated using a motor as disclosed in U.S. Pat. Nos. 4,666,647, 4,761,258, or 6,202,259. The forming fabric 34 can be made of various materials, such as plastic or metal.

As shown, the airlaying forming station 30 includes a forming chamber 44 having end walls and side walls. Within the forming chamber 44 are a pair of material distributors 46 and 48 which distribute fibers inside the forming chamber 44 across the width of the chamber. The material distributors 46 and 48 can be, for instance, rotating cylindrical distributing screens.

In the embodiment shown in FIG. 1, a single forming chamber 44 is illustrated in association with the forming fabric 34. It should be understood, however, that more than one forming chamber can be included in the system. By including multiple forming chambers, layered webs can be formed in which each layer is made from the same or different materials.

Airlaying forming stations as shown in FIG. 1 are available commercially through Dan-Webforming Int. LTD. of Aarhus, Denmark. Other suitable airlaying forming systems are also available from M & J Fibretech of Horsens, Denmark. In general, any suitable airlaying forming system can be used in accordance with the present invention.

As shown in FIG. 1, below the airlaying forming station 30 is a vacuum source 50, such as a conventional blower, for creating a selected pressure differential through the forming chamber 44 to draw the fibrous material against the forming fabric 34. If desired, a blower can also be incorporated into the forming chamber 44 for assisting in blowing the fibers down on to the forming fabric 34.

In one embodiment, the vacuum source 50 is a blower connected to a vacuum box 52 which is located below the forming chamber 44 and the forming fabric 34. The vacuum source 50 creates an airflow indicated by the arrows positioned within the forming chamber 44. Various seals can be used to increase the positive air pressure between the chamber and the forming fabric surface.

During operation, the fiber stock is fed to one or more defibrators (not shown) and fed to the material distributors 46 and 48. The material distributors distribute the fibers evenly throughout the forming chamber 44 as shown. Positive airflow created by the vacuum source 50 and possibly an additional blower force the fibers onto the forming fabric 34 thereby forming an airlaid non-woven web 32.

When forming the airlaid web 32 from different fibers, the forming chamber 44 can include multiple inlets for feeding the materials to the chamber. Once in the chamber, the materials can be mixed together if desired.

Figure 2:
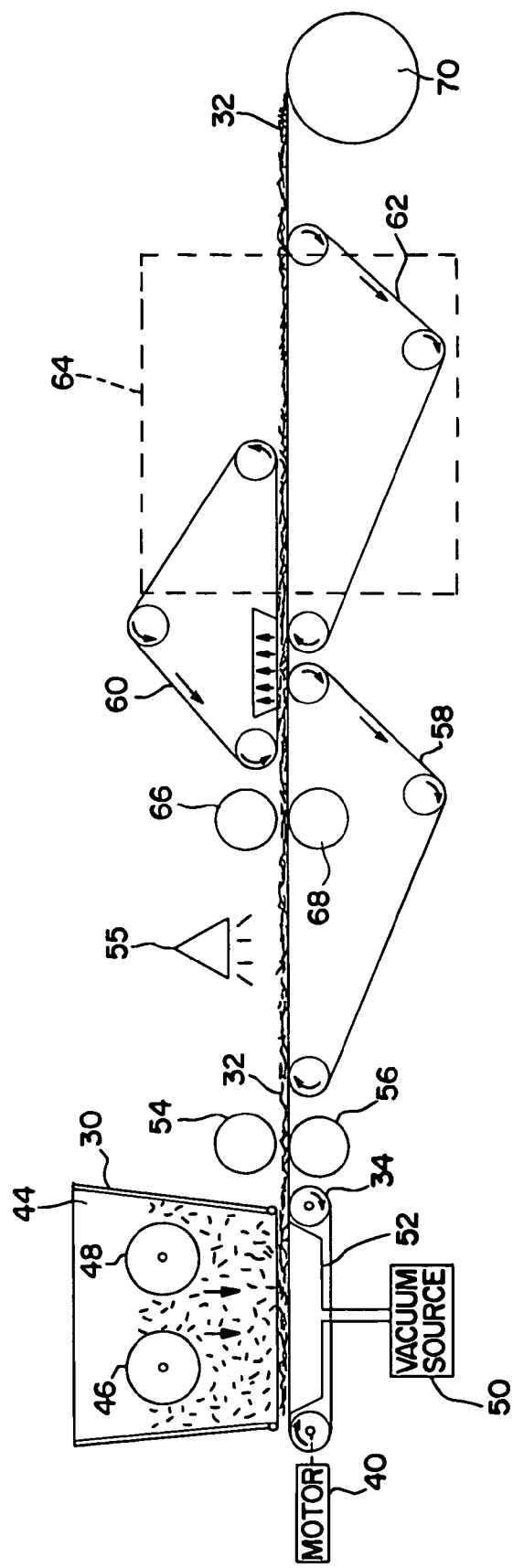
FIG. 2 is a simplified side view of a system for forming airlaid nonwoven webs in accordance with the present invention.

Referring to FIG. 2, one embodiment of an entire web forming system incorporating the airlaying station 30 of FIG. 1 is shown. In this embodiment, the airlaid web 32 is formed under the airlaying forming station 30 on a forming fabric 34. From the forming fabric 34, the web 32 is fed to and supported by a transfer fabric 58. While on the transfer fabric 58, a shower head 55 is used to spray an aqueous solution onto the nonwoven web 32. The aqueous solution may be, for instance, pure water. The aqueous solution may be sprayed as a mist onto the surface of the web causing the polyvinyl alcohol fibers to become tacky. The amount of aqueous solution sprayed on the web may vary depending upon the particular application and the amount of polyvinyl alcohol fibers contained within the web. In one embodiment, for instance, the aqueous solution may be sprayed onto the web in an amount of from about 5% to about 30% by weight of the web, such as from about 10% to about 20% by weight. By making the polyvinyl alcohol fibers tacky, the fibers are then prone to bond with each other and to the pulp fibers. In this manner, the integrity and strength of the web is increased.

From the transfer fabric 58, the airlaid web 32 is then guided onto a drying fabric 62 with the help of a second transfer fabric 60. As shown in FIG. 2, a suction device may be used to assist in transferring the nonwoven web 32 from the transfer fabric 58 to the drying fabric 62.

As shown by the dotted lines in FIG. 2, the system may further include a drying device 64. The drying device 64 is for drying the nonwoven web 32 while traveling on the drying fabric 62. The drying device may be, for instance, a convective oven that circulates hot air or a through-air dryer. The through-air dryer may, for instance, circulate hot air above and below the nonwoven web 32 for drying the web.

While in the drying device 64, the airlaid nonwoven web 32 is heated to a temperature sufficient to evaporate any moisture contained in the web. For instance, the web may be heated to a temperature of from about 200° F. to about 250° F.

After passing through the drying device 64, the airlaid nonwoven web 32 is then wound onto a reel 70 for later converting into, for example, a pre-saturated wiping product.

In one embodiment, in order to further increase the strength of the airlaid nonwoven web 32, the web may be embossed. For instance, the web may be embossed after being wetted with an aqueous solution. For instance, as shown in FIG. 2, the process may include embossing rollers 66 and 68 that emboss a pattern into the web. Embossing the web 32 after being wetted further facilitates bonding between the water soluble fibers and the pulp fibers.

In general, any suitable pattern may be embossed into the web. For instance, the embossing pattern may comprise a grid comprised of geometric shapes. The embossing rollers 66 and 68 form densified regions in the web as the web is embossed. In one embodiment, the densified regions may be spaced from each other no farther than about two times the average length of the fibers contained in the web. For example, in one embodiment, the largest dimension of an individual cell contained in the grid pattern is less than about 10 mm, such as less than about 5 mm.

In an alternative embodiment, instead of embossing a grid into the nonwoven web 32, discrete shapes may be embossed into the pattern. The discrete shapes form point bonds between the fibers.

As shown in FIG. 2, instead of embossing the airlaid nonwoven web 32 after application of the aqueous solution, in still another embodiment of the present invention, the web 32 may be embossed prior to application of the aqueous solution. For instance, the nonwoven web 32 may be embossed by embossing rollers 54 and 56. In this embodiment, the embossing rollers 54 and 56 form channels where the aqueous solution collects when later applied. In this manner, the densified regions caused by the embossing rollers serve to increase the strength of the web.

Instead of embossing a pattern into the web, it should also be understood that the web may be calendered instead. For instance, the rollers 54 and 56 and the rollers 66 and 68 may comprise calender rolls if desired.

The basis weight of the airlaid nonwoven web 32 prior to being saturated with a cleaning solution may vary greatly depending upon the end use application. For example, the basis weight may range from about 20 gsm to about 120 gsm, such as from about 40 gsm to about 80 gsm. In one particular embodiment, for instance, the basis weight may range from about 60 gsm to about 70 gsm (at ambient conditions).

After the airlaid nonwoven web is formed, the web is then impregnated with a cleaning solution for use as a wiping product. The cleaning solution is for cleaning and/or disinfecting a surface. In one embodiment, the cleaning solution may comprise water and an alcohol. The alcohol may be, for instance, an aliphatic alcohol having from about 1 to about 6 carbon atoms. By way of example, the alcohol may be methanol, ethanol, propanol, isopropanol, butanol, t-butanol, 2-butanol, pentanol, 2-pentanol, hexanol, 2,3-dimethyl-1-butanol, and the like, including mixtures of two or more alcohols.

In general, the cleaning solution should contain water in an amount less than about 50% by weight. For instance, in one embodiment, the solution may contain alcohol in an amount greater than about 60% by weight, such as from about 60% by weight to about 80% by weight. Greater amounts of alcohol, however, may be used.

In addition to water and an alcohol, the cleaning solution may also contain various other additives. Such other additives include disinfectants, antiseptics, emollients, skin conditioners, anti-microbial agents such as sterilants, sporicides, germicides, bactericides, fungicides, virucides, protozoacides, algicides, bacteriostats, fungistats, virustats, sanitizers, and antibiotics, fragrances, anti-drying agents, and the like.

Example of anti-drying agents include glycols and glycerides. Examples of anti-microbial agents, on the other hand, include quaternary ammonium compounds, such as quaternary ammonium halide compounds. In some embodiments, quaternary ammonium halide compounds having the following formula are utilized:

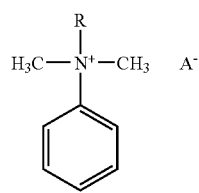

wherein,

R is a $C_8$-$C_{18}$ alkyl group; and

A is a halogen atom, such as chlorine, bromine, fluorine, and the like.

One commercially available example of an antimicrobial agent that includes such a quaternary ammonium compound is available under the trade name BARDAC® 208M from Lonza, Inc., Fairlawn, N.J. Specifically, BARDAC® 208M contains a blend of alkyl dimethyl benzyl ammonium chlorides. Other commercially available examples of suitable quaternary ammonium compounds are believed to include BARDAC® 2050 and BARDAC® 2080 (based on dialkyl ($C_8$-$C_{10}$)dimethyl ammonium chloride); BARDAC® 2250 and BARDAC® 2280 (didecyl dimethyl ammonium chloride); BARDAC® LF and BARDAC® LF 80 (based on dioctyl dimethyl ammonium chloride); BARQUAT® MB-50 and BARQUAT® MB-80 (based on alkyl dimethyl benzyl ammonium chloride); BARQUAT® MX-50 and BARQUAT® MX-80 (based on alkyl dimethyl benzyl ammonium chloride); BARQUAT® OJ-50 and BARQUAT® OJ-80 (based on alkyl dimethyl benzyl ammonium chloride); BARQUAT® 4250, BARQUAT® 4280, BARQUAT® 4250Z, and BARQUAT® 4280Z (based on alkyl dimethyl benzyl ammonium chloride and/or alkyl dimethyl ethyl benzyl ammonium chloride); and BARQUAT® MS-100 (based on myristyl dimethyl benzyl ammonium chloride), which are available from Lonza, Inc., Fairlawn, N.J.

Other anti-microbial agents that may be used in the present invention include halogenated diphenyl ethers like 2,4,4'-trichloro-2'-hydroxy-diphenyl ether (Triclosan® or TCS) or 2,2'-dihydroxy-5,5'-dibromo-diphenyl ether; phenolic compounds like phenoxyethanol, phenoxy propanol, phenoxyisopropanol, para-chloro-meta-xylenol (PCMX), etc.; bisphenolic compounds like 2,2'-methylene bis (4-chlorophenol), 2,2'-methylene bis(3,4,6-trichlorophenol), 2,2'-methylene bis(4-chloro-6-bromophenol), bis(2-hydroxy-3,5-dichlorophenyl) sulphide, and bis(2-hydroxy-5-chlorobenzyl)sulphide; halogenated carbanilides (e.g., 3,4,4'-trichlorocarbanilides (Triclocarban® or TCC); benzyl alcohols; chlorhexidine; chlorhexidine gluconate; and chlorhexidine hydrochloride.

The cleaning solution impregnated into the airlaid nonwoven web may also contain one or more surfactants. Surfactants can provide a number of benefits to the resulting wiper. For instance, surfactants can increase the wettability of the wiping product, can serve as emollients, can improve the ability of the wiping product to clean surfaces, and can also serve to stabilize the cleaning solution itself. In general, any suitable nonionic, anionic, cationic and amphoteric surfactant may be incorporated into the cleaning solution.

In some embodiments, the cleaning solution can also contain one or more preservatives. Suitable preservatives include, for instance, Kathon CG®, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

In general, any of the above additives may be present in the cleaning solution in an amount less than about 20% by weight, such as less than about 5% by weight. For instance, many of the additives may be present in an amount from about 0.001% to about 2% by weight.

Once the airlaid nonwoven web is impregnated with a cleaning solution, the wiping products may be packaged as desired. For instance, the wiping product may be packaged in a resealable container. Some examples of suitable containers include rigid tubs, film pouches, etc. One particular example of a suitable container for holding the wipers is a rigid, cylindrical tub (e.g., made from polyethylene) that is fitted with a resealable air-tight lid on the top portion of the container. The lid has a hinged cap initially covering an opening positioned beneath the cap. The opening allows for the passage of wipers from the interior of the sealed container whereby individual wipers can be removed by grasping the wiper.

In another embodiment, the wiper may be held in a liquid impermeable pouch that has an ovular shaped opening. The opening may be covered by a tab that is attached to the pouch by a pressure sensitive adhesive. The tab may be opened to remove a wiper and then resealed against the pouch.

The pre-saturated wipers may be cut into individual sheets that are folded and stacked together. In an alternative embodiment, the wiping product may be spirally wound to form a roll. In this embodiment, the individual wipers may be separated by a perforation.

When removed from the container, the wiping product contains a sufficient amount of a cleaning solution to clean and/or disinfect a surface. After being used, the wiping product can then be disposed. Of particular advantage, since the wiper is water dispersible, the wiper may be flushed down a commode after use.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A water dispersible, pre-saturated wiping product comprising:
   a nonwoven airlaid fibrous web, the airlaid web comprising pulp fibers and water soluble fibers, the water soluble fibers comprising polyvinyl alcohol, the water soluble fibers being substantially soluble in water at temperatures of less than about 10° C., the water soluble fibers being present in the airlaid web in an amount sufficient to make the web water dispersible such that the web disintegrates when immersed in water; and
   a cleaning solution impregnated into the airlaid web.

2. A wiping product as defined in claim 1, wherein the polyvinyl alcohol contained in the water soluble fibers is less than about 95% hydrolyzed, the polyvinyl alcohol containing vinyl acetate units.

3. A wiping product as defined in claim 1, wherein the polyvinyl alcohol contained in the water soluble fibers is less than about 90% hydrolyzed, the polyvinyl alcohol containing vinyl acetate units.

4. A wiping product as defined in claim 2, wherein the polyvinyl alcohol is at least 80% hydrolyzed.

5. A wiping product as defined in claim 1, wherein the water soluble fibers are bonded to the pulp fibers.

6. A wiping product as defined in claim 1, wherein the pulp fibers comprise softwood fibers.

7. A wiping product as defined in claim 1, wherein the water soluble fibers have an average length of less than about 8 mm.

8. A wiping product as defined in claim 1, wherein the water soluble fibers have an average length of from about 2 mm to about 8 mm.

9. A wiping product as defined in claim 1, wherein the water soluble fibers are present within the airlaid fibrous web in an amount from about 10% to about 80% by weight prior to being impregnated with the cleaning solution.

10. A wiping product as defined in claim 1, wherein the water soluble fibers are present within the airlaid fibrous web in an amount from about 15% to about 35% by weight prior to being impregnated with the cleaning solution.

11. A wiping product as defined in claim 1, wherein the nonwoven airlaid fibrous web has a basis weight of from about 20 gsm to about 120 gsm prior to being impregnated with the cleaning solution.

12. A wiping product as defined in claim 1, wherein the nonwoven airlaid fibrous web has a basis weight of from about 40 gsm to about 80 gsm prior to being impregnated with the cleaning solution.

13. A wiping product as defined in claim 1, wherein the nonwoven airlaid fibrous web has been embossed.

14. A wiping product as defined in claim 1, wherein the cleaning solution further comprises an alcohol and water, the alcohol being present in the cleaning solution in an amount of at least 60% by weight.

15. A wiping product as defined in claim 14, wherein the alcohol is contained in the cleaning solution in an amount from about 70% to about 90% by weight.

16. A resealable dispensing container containing the water dispersible, pre-saturated wiping product as defined in claim 1.

17. A wiping product as defined in claim 1, wherein the wiping product comprises a plurality of stacked, individual sheets.

18. A wiping product as defined in claim 1, wherein the wiping product comprises a spirally wound roll of individual sheets separated by perforations.

19. A wiping product as defined in claim 15, wherein the alcohol comprises ethyl alcohol or isopropyl alcohol.

20. A wiping product as defined in claim 1, wherein the cleaning solution further comprises at least one surfactant.

21. A wiping product as defined in claim 1, wherein the cleaning solution further comprises a glycol or a glyceride.

22. A wiping product as defined in claim 1, wherein the cleaning solution further comprises an antimicrobial agent.

23. A wiping product as defined in claim 1, wherein the cleaning solution further comprises a fragrance.

24. A wiping product as defined in claim 1, wherein the pulp fibers and the water soluble fibers are homogenously distributed throughout the nonwoven airlaid fibrous web.

25. A nonwoven material comprising:
    an airlaid fibrous web containing a mixture of pulp fibers and polyvinyl alcohol fibers, the polyvinyl alcohol fibers being substantially soluble in water at temperatures of less than about 10° C., the polyvinyl alcohol fibers having a length of less than about 8 mm, the polyvinyl alcohol fibers being bonded to the pulp fibers, the polyvinyl alcohol fibers being present in the airlaid fibrous web in an amount of at least 10% by weight such that the web disintegrates when immersed in water, and
    a cleaning solution integral to the airlaid fibrous web.

26. A nonwoven material as defined in claim 25, wherein the polyvinyl alcohol fibers comprise a polyvinyl alcohol that is less than about 95% hydrolyzed, the polyvinyl alcohol containing vinyl acetate units.

27. A nonwoven material as defined in claim 25, wherein the polyvinyl alcohol fibers comprise a polyvinyl alcohol that is less than about 90% hydrolyzed, the polyvinyl alcohol containing vinyl acetate units.

28. A nonwoven material as defined in claim 26, wherein the polyvinyl alcohol is hydrolyzed in an amount greater than about 80%.

29. A nonwoven material as defined in claim 25, wherein the pulp fibers comprise softwood fibers.

30. A nonwoven material as defined in claim 25, wherein the polyvinyl alcohol fibers have an average length of from about 2 mm to about 8 mm.

31. A nonwoven material as defined in claim 25, wherein the airlaid fibrous web has a basis weight of from about 20 gsm to about 120 gsm.

32. A nonwoven material as defined in claim 25, wherein the airlaid fibrous web has a basis weight of from about 40 gsm to about 80 gsm.

33. A nonwoven material as defined in claim 25, wherein the airlaid fibrous web has been embossed.

34. A water dispersible, pre-saturated wiping product comprising:
    a nonwoven airlaid fibrous web, the airlaid fibrous web comprising a mixture of pulp fibers and polyvinyl alcohol fibers, the pulp fibers comprising softwood fibers, the polyvinyl alcohol fibers being substantially soluble in water at temperatures of less than about 10° C., the polyvinyl alcohol fibers having an average fiber length of less than about 8 mm and being present in the airlaid fibrous web in an amount of at least about 10% by weight such that the web disintegrates when immersed in water, the polyvinyl alcohol fibers being bonded to the pulp fibers; and
    a cleaning solution impregnated into the airlaid web, the cleaning solution comprising water and an alcohol, the alcohol being present in the cleaning solution in an amount of at least 60% by weight.

35. A wiping product as defined in claim 34, wherein the polyvinyl alcohol fibers are substantially soluble in water at a temperature of less than about 5° C.

36. A wiping product as defined in claim 34, wherein the polyvinyl alcohol contained in the water soluble fibers is less than about 95% hydrolyzed, the polyvinyl alcohol containing vinyl acetate units.

37. A wiping product as defined in claim 34, wherein the polyvinyl alcohol contained in the water soluble fibers is less than about 90% hydrolyzed, the polyvinyl alcohol containing vinyl acetate units.

38. A wiping product as defined in claim 36, wherein the polyvinyl alcohol is at least 80% hydrolyzed.

39. A wiping product as defined in claim 34, wherein the polyvinyl alcohol fibers have an average fiber length of from about 2 mm to about 8 mm.

40. A wiping product as defined in claim 34, wherein the polyvinyl alcohol fibers are present in the nonwoven airlaid fibrous web in an amount from about 15% to about 35% by weight prior to being impregnated with the cleaning solution.

41. A wiping product as defined in claim 34, wherein the nonwoven airlaid fibrous web has a basis weight of from about 20 gsm to about 120 gsm prior to being impregnated with the cleaning solution.

42. A wiping product as defined in claim 34, wherein the nonwoven airlaid fibrous web has a basis weight of from about 40 gsm to about 80 gsm prior to being impregnated with the cleaning solution.

43. A wiping product as defined in claim 34, wherein the nonwoven airlaid fibrous web has been embossed.

44. A wiping product as defined in claim 34, wherein the alcohol is contained in the cleaning solution in an amount from about 70% to about 90% by weight.

45. A resealable dispensing container containing the water dispersible, pre-saturated wiping product as defined in claim 34.

46. A wiping product as defined in claim 34, wherein the wiping product comprises a plurality of stacked, individual sheets.

47. A wiping product as defined in claim 34, wherein the wiping product comprises a spirally wound roll of individual sheets separated by perforations.

48. A wiping product as defined in claim 34, wherein the alcohol comprises ethyl alcohol or isopropyl alcohol.

* * * * *